(12) United States Patent
Cooper et al.

(10) Patent No.: US 10,849,780 B2
(45) Date of Patent: Dec. 1, 2020

(54) ARM IMMOBILIZATION APPARATUS AND METHODS FOR WEARING THE APPARATUS

(71) Applicant: Avalanche Studio Pte Ltd, Asap (SG)

(72) Inventors: Anthony James Cooper, Asap (SG); Abhishek Dushyant Mohla, Maplewoods (SG)

(73) Assignee: AVALANCHE STUDIO PTE LTD, Asap (SG)

( * ) Notice: Subject to any disclaimer, the term of this patent is extended or adjusted under 35 U.S.C. 154(b) by 496 days.

(21) Appl. No.: 15/560,589

(22) PCT Filed: Feb. 3, 2016

(86) PCT No.: PCT/SG2016/050055
§ 371 (c)(1),
(2) Date: Sep. 22, 2017

(87) PCT Pub. No.: WO2016/153424
PCT Pub. Date: Sep. 29, 2016

(65) Prior Publication Data
US 2018/0104086 A1    Apr. 19, 2018

(30) Foreign Application Priority Data

Mar. 24, 2015    (WO) ................ PCT/SG2015/000090

(51) Int. Cl.
*A61F 5/37*    (2006.01)
(52) U.S. Cl.
CPC ............ *A61F 5/373* (2013.01); *A61F 5/3723* (2013.01); *A61F 5/3738* (2013.01)

(58) Field of Classification Search
CPC .... A61F 5/3738; A61F 5/3753; A61F 5/3723; A61F 5/3746; A61F 2/0045; A61F 5/0118; A61F 5/3715; A61F 2230/0019; A61F 5/373; A61F 5/37; A61F 13/10; A61F 5/00; A61F 5/0193; A61F 5/028; A61F 5/04; A61F 5/3761
See application file for complete search history.

(56) References Cited

U.S. PATENT DOCUMENTS 1,745,446 A    2/1930 Payne
4,198,964 A    4/1980 Honneffer
(Continued)

FOREIGN PATENT DOCUMENTS

EP    2591757 A1    5/2013
WO    WO 2017/027737 A1    2/2017

OTHER PUBLICATIONS

International Search Report and Written Opinion in corresponding PCT Application No. PCT/SG2016/050055, dated Mar. 16, 2016.
(Continued)

*Primary Examiner* — Ophelia A Hawthorne
(74) *Attorney, Agent, or Firm* — Leason Ellis LLP (57) ABSTRACT

An arm immobilization apparatus (800) is disclosed, which comprises a main body (802) arranged to be of a substantially oblong shape; and a location strap (804) having first and second ends (806*a*, 806*b*), wherein the first end is arranged to be coupled to a long edge of the main body, and the second end is coupled to first and second short edges (808*a*, 808*b*) of the main body. Corresponding methods for wearing the arm immobilization apparatus are also disclosed.

18 Claims, 12 Drawing Sheets

(56) References Cited

U.S. PATENT DOCUMENTS

| | | | |
|---|---|---|---|
| 4,598,702 A * | 7/1986 | Lilla | A61F 5/3738 |
| | | | 602/4 |
| 4,834,082 A | 5/1989 | Ghadiali | |
| 4,844,306 A * | 7/1989 | Ruff | A61B 5/02233 |
| | | | 224/600 |
| 4,895,142 A | 1/1990 | Liptak | |
| 7,749,179 B2 * | 7/2010 | Hargrave | A61F 5/3753 |
| | | | 224/157 |
| 2003/0187373 A1 | 10/2003 | Gaylord | |
| 2006/0258966 A1 | 11/2006 | Hargrave et al. | |
| 2006/0270957 A1 * | 11/2006 | Hollister | A61F 5/3738 |
| | | | 602/4 |
| 2008/0119770 A1 | 5/2008 | Miller et al. | |
| 2015/0080776 A1 * | 3/2015 | Davis | A61F 5/3738 |
| | | | 602/4 |
| 2018/0228637 A1 | 8/2018 | Elzik et al. | |

OTHER PUBLICATIONS

Extended European Search Report in corresponding European Application No. 16769177.3, dated Dec. 3, 2018.
International Preliminary Report on Patentability in corresponding PCT Application No. PCT/SG2015/000090, dated Sep. 1, 2015.
Extended European Search Report in corresponding European Application No. 16769177.3, dated Nov. 20, 2018.

* cited by examiner

ARM IMMOBILIZATION APPARATUS AND METHODS FOR WEARING THE APPARATUS

CROSS-REFERENCE TO RELATED PATENT APPLICATIONS

This application is a U.S. National Phase Application under 35 U.S.C. § 371 of International Patent Application No. PCT/SG2016/050055, filed Feb. 3, 2016, and claims the priority of International Application No. PCT/SG2015/000090, filed Mar. 24, 2015, all of which are incorporated by reference in their entireties. The International Application was published on Sep. 9, 2016 as International Publication No. WO 2016/153424 A1.

FIELD OF INVENTION

The present invention relates to an arm immobilization apparatus which is usable for various purposes and methods to wear the apparatus.

BACKGROUND

There are several designs currently available for apparatus used to immobilize an arm (typically referred to as slings). The designs range from those using a triangular bandage to those with an arm holder and a fastening strap(s). However, the current designs include flaws/limitations which have not been addressed despite an extended duration of availability in the market.

One of the issues for the current designs in the market relates to how the slings merely support the arm and does not adequately prevent movement of the arm. Essentially, the current designs in the market do not provide holistic immobilization pertaining to the injured arm.

Another issue for the current designs in the market relates to how extended use leads to significant discomfort at the neck and/or shoulder blades of the user because of the substantial loading the neck and/or shoulder blades undergoes when the arm is placed in the sling. This is because of strap design of the current designs in the market which apply substantial stresses to the neck and/or should blades during use. Furthermore, the straps used in the current designs in the market also require regular re-adjustment, re-attachment, re-strapping after extended usage. This constant need for adjustment and/or intervention is inconvenient and burdensome for the user.

Furthermore, in circumstances when the user has an arm which is completely/significantly dysfunctional, yet another issue for the current designs relates to difficulty of putting on a sling without assistance from a third party. This comprises an ability of the user to administer self-care in the absence of third parties.

Moreover, even though current designs provide support for the arm, they typically do not provide sufficient support for the shoulder and the elbow, and this inadequacy may lead to shoulder subluxation. In addition, thin straps used for current designs exert localized pressure and unfortunately cause discomfort to the user over an extended duration of time.

Finally, it should also be noted that current designs are typically constructed/fabricated in a manner which is not robust and prone to wear and tear leading to a short duration of use before replacement and/or adjustment becomes necessary.

Thus, it should be noted that the current designs have issues.

SUMMARY

According to a $1^{st}$ aspect of the invention, there is provided an arm immobilization apparatus comprising: a main body arranged to be of a substantially oblong shape; and a location strap having first and second ends, wherein the first end is arranged to be coupled to a long edge of the main body, and the second end is coupled to first and second short edges of the main body.

Preferably, the first end may include being adjustably couplable to the long edge of the main body.

Preferably, the apparatus may further include a quick release device at the first end to enable the first end to be adjustably couplable to the main body.

Preferably, the second end may include being movably coupled to the first and second short edges of the main body.

Preferably, the second end may movably be coupled to the first and second short edges of the main body via a ring. It is to be appreciated that other suitable implements are also possible that enable the second end, and the first and second short edges to be movably coupled together.

Preferably, the second end may alternatively include being attached to the first and second short edges of the main body.

Preferably, the main body may comprise first and second portions, in which at least the first portion is adjustably coupled to the second portion to enable a length of the main body to be configurable.

Preferably, the first and second portions may include at least one fastening device respectively. Preferably, the main body may alternatively be integrally formed.

Preferably, the first short edge of the main body may be configured to be coupled to the second short edge of the main body.

Preferably, the apparatus may further include a compartment for placement of an arm of a user of the apparatus.

Preferably, the compartment may be formed using a non-stretchable fabric or a stretchable fabric configured to enable dissipation of heat from within the compartment. It is to be appreciated that the non-stretchable fabric includes standard fabric/cotton-based fabric that are typically used for manufacturing conventional arm slings.

Preferably, the location strap may have a variable length.

Preferably, the main body may be fabricated from a hard-wearing, lightweight and flexible fabric.

Preferably, the location strap may be configured for mounting the apparatus in multiple positions.

Preferably, the apparatus may further comprise at least one device configured to carry out at least one task for determining a condition or a state of activity of a user of the apparatus.

According to a $2^{nd}$ aspect of the invention, there is provided a method for wearing the arm immobilization apparatus of the $1^{st}$ aspect, the method comprising: placing an arm of a user into the compartment; wearing the main body on the body of the user; and positioning the location strap of the apparatus under an armpit of the user.

According to a $3^{rd}$ aspect of the invention, there is provided a method for wearing the arm immobilization apparatus of the $1^{st}$ aspect, the method comprising: positioning the location strap of the apparatus under an armpit of a user; wearing the main body on the body of the user; and securing the arm of the user to the main body.

Preferably, positioning the location strap of the apparatus may include adjustably coupling the first end of the location strap to the long edge of the main body.

DESCRIPTION OF FIGURES

In order that the present invention may be fully understood and readily put into practical effect, there shall now be described by way of non-limitative example only preferred embodiments of the present invention, the description being with reference to the accompanying illustrative figures.

FIG. 8 includes FIGS. 8a-8c, which respectively shows a front view, a side view, and a back view of an apparatus, according to a second embodiment.

FIG. 9 includes FIGS. 9a-9c, which respectively are full image renderings of FIGS. 8a-8c.

FIG. 11 includes FIGS. 11a-11c, which are respective photographs showing a front view, a side view, and a back view of an apparatus, according to a third embodiment.

DESCRIPTION OF PREFERRED EMBODIMENTS

Figure 1:
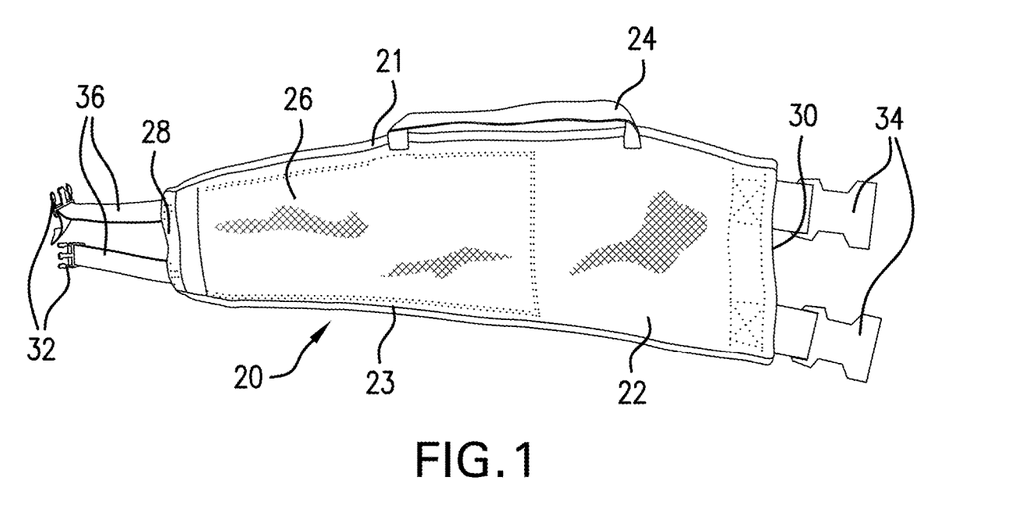
FIG. 1 is a photograph of a first view of an apparatus, according to a first embodiment.
Figure 2:
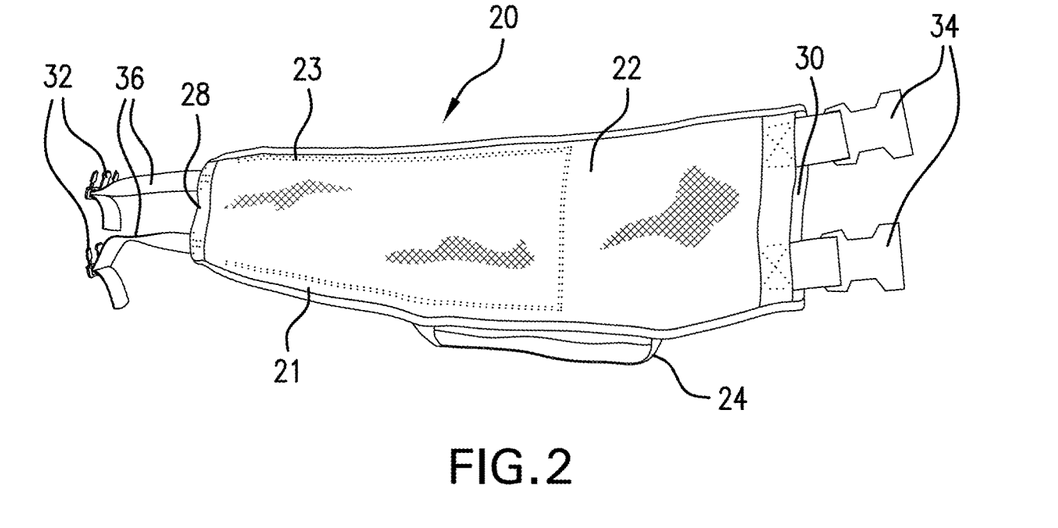
FIG. 2 is a photograph of a second view of the apparatus of FIG. 1.

Reference is made to the Figures to describe preferred embodiments of the apparatus of the present invention. FIGS. 1 and 2 show different views of the apparatus, while FIGS. 3 to 6 show different views of the apparatus during use.

There is provided an arm immobilization apparatus 20, according to a first embodiment. The apparatus 20 can be used for various purposes such as, for example, physical rehabilitation, disability therapy, medical treatment, sports, day-to-day regular activities, and so forth. The apparatus 20 is able to function as more than a typical arm sling, as will be evident in the subsequent paragraphs. The apparatus 20 comprises a main body 22 being of a substantially oblong shape. Specifically, the substantially oblong shape of the main body 22 provides a sleek streamlined design for the apparatus 20 and this can also minimize weight and amount of material being used. The main body 22 is fabricated from a hard-wearing, lightweight and flexible fabric. Suitable fabrics can be made from naturally occurring materials or synthetic materials demonstrating the aforementioned desired properties.

The apparatus 20 also includes a location strap 24 attached to the main body 22. The location strap 24 is used to mount the apparatus 20 at desired portion of a user's body and also to prevent the apparatus 20 from moving/sliding during use of the apparatus 20. This will be described in greater detail when describing the use of the apparatus 20. The location strap 24 as shown is attached to the main body 22 which causes difficulty in removing the location strap 24 from the main body 22. However, the location strap 24 can also be attached to the main body 22 in a manner which enables ease of removal in-situ such that the location strap 24 can be re-located to another position on the main body 22. For example, the location strap 24 is shown to be attached to a first long edge 21, but the location strap 24 can also be attached to a second long edge 23. This allows the apparatus 20 to be usable with both a left arm and a right arm of the user. Moreover, the location strap 24 can have a variable length to enable it to be customizable for needs of any user, because the location strap 24 can be either elastic (as shown) or adjustable length-wise.

In addition, the apparatus 20 can also include a compartment 26 for placement of the arm which is being immobilized. The compartment 26 can be a sleeve made using a stretchable fabric, the stretchable fabric being able to allow dissipation of heat from within the compartment 26. The compartment 26 is sized to accommodate the arm up to an elbow portion. The sleeve should not conform too tightly to the arm as this may cause discomfort to the user. It is advantageous for the sleeve to be made using the stretchable fabric as a portion of the arm may be encased within a cast, and the stretchable fabric allows the arm encased within the cast to be placed within the sleeve. Instead of the compartment 26, it may be possible to use at least two straps to secure the arm to the main body 22. The at least two straps can be attachable to the main body 22, or they can be standalone and used to secure the arm which is being immobilized to the main body 22.

In the apparatus 20, a first short edge 28 of the main body 22 is configured to be secured to a second short edge 30 of the main body 22. In the Figures, the first short edge 28 and the second short edge 30 are shown to have a pair of fastening mechanisms 32, 34 respectively such that the edges 28, 30 are able to be secured to one another at a back of the user. In this instance, even though two sets of fastening clips are used as the fastening mechanisms 32, 34, it can be possible for a single fastening clip to be used. In addition, while the edges 28, 30 are not shown to overlap in this instance, if other forms of fastening mechanisms are used, then it can be possible for the edges 28, 30 to overlap. When the edges 28, 30 overlap, there is no necessity for straps 36.

Furthermore, the apparatus 20 can also include at least one device such as, for example, at least one sensor, a transmitter and so forth. The devices can be configured to perform at least one task such as, for example, detection, recordal, analysis, transmission of the user's condition and/or state of activity.

Referring to FIGS. 3 to 6, there is shown different views of the apparatus 20 during use. As mentioned earlier, the location strap 24 aids the user 18 in positioning the apparatus 20 to rest on a desirable portion of the user's 18 body prior to securing the apparatus 20 to the user's 18 body. Once the location strap 24 is positioned under an armpit of the user, the armpit being on an opposite side of the arm being immobilized, the user 18 can then start to secure the apparatus 20 to his/her body as the apparatus 20 would be in a desirable position for securing at that juncture. The location strap 24 can be thicker than that as shown in the Figures to spread out pressure applied to the armpit of the user. The location strap 24 can have variable degrees of flexibility to enhance comfort at the armpit of the user. Once the apparatus 20 is in the desirable position, the user 18 is able to cause the edges 28, 30 to be secured to one another without assistance from third parties, as the user 18 is able to use the free arm to cause the edges 28, 30 to be secured to one another. One possibility of carrying out the task is by securing the fastening mechanism 32, 34 before adjusting a length of the straps 36 to ensure a comfortable fit. In this regard, the apparatus 20 is able to facilitate an independent lifestyle for the user 18.

Figure 3:
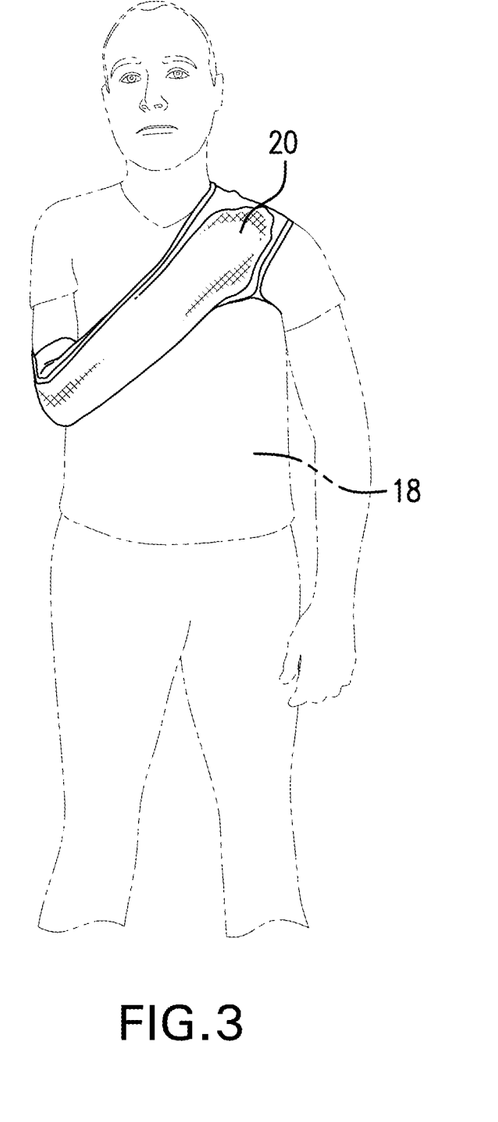
FIG. 3 is a photograph of a front view of a user of the apparatus of FIG. 1 during use.
Figure 4:
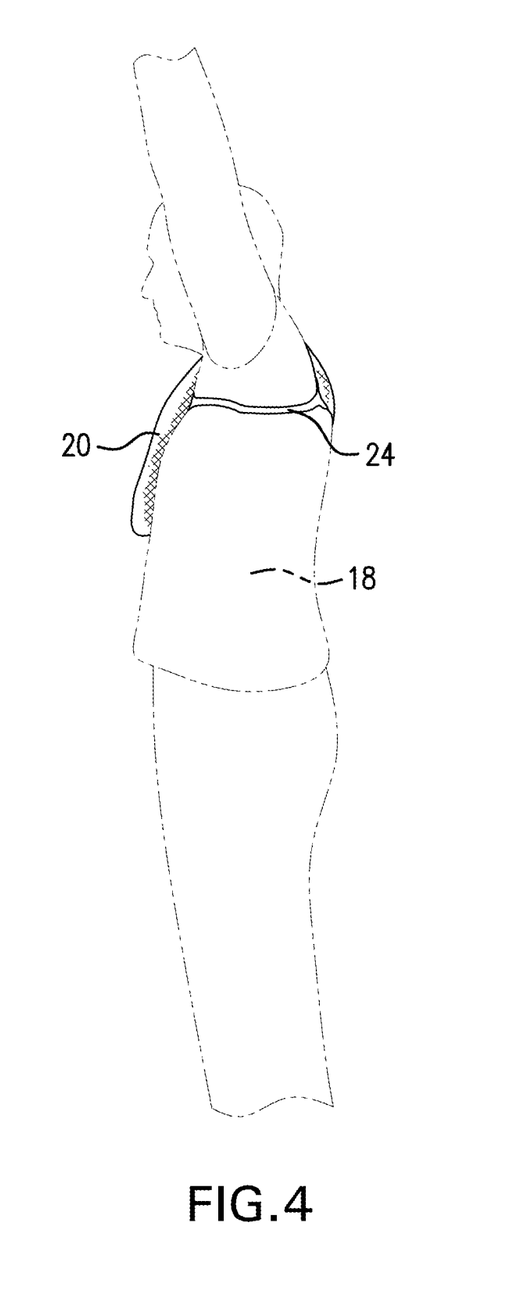
FIG. 4 is a photograph of a left view of the user of the apparatus of FIG. 1 during use.
Figure 5:
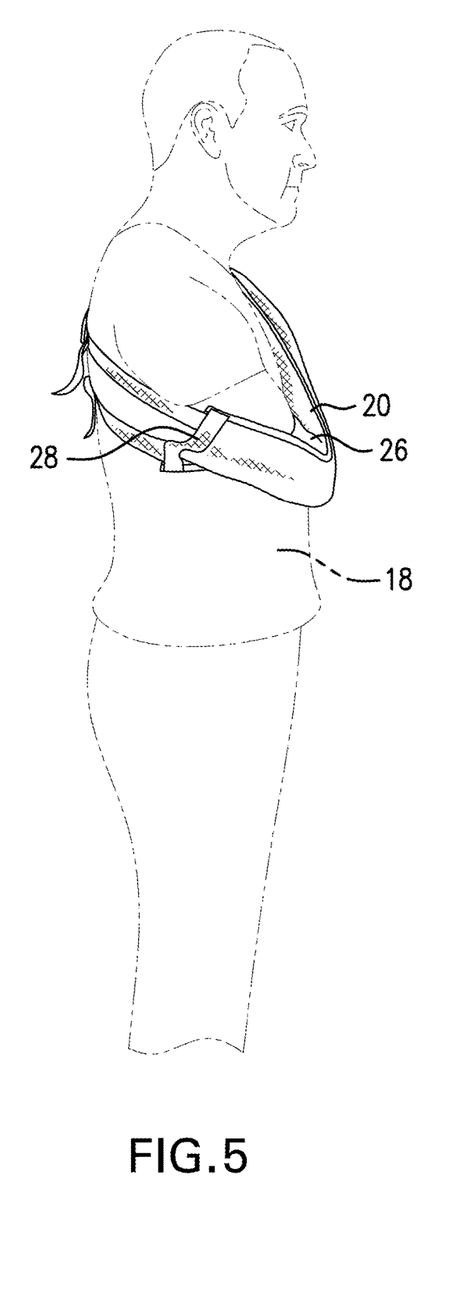
FIG. 5 is a photograph of a right view of the user of the apparatus of FIG. 1 during use.
Figure 6:
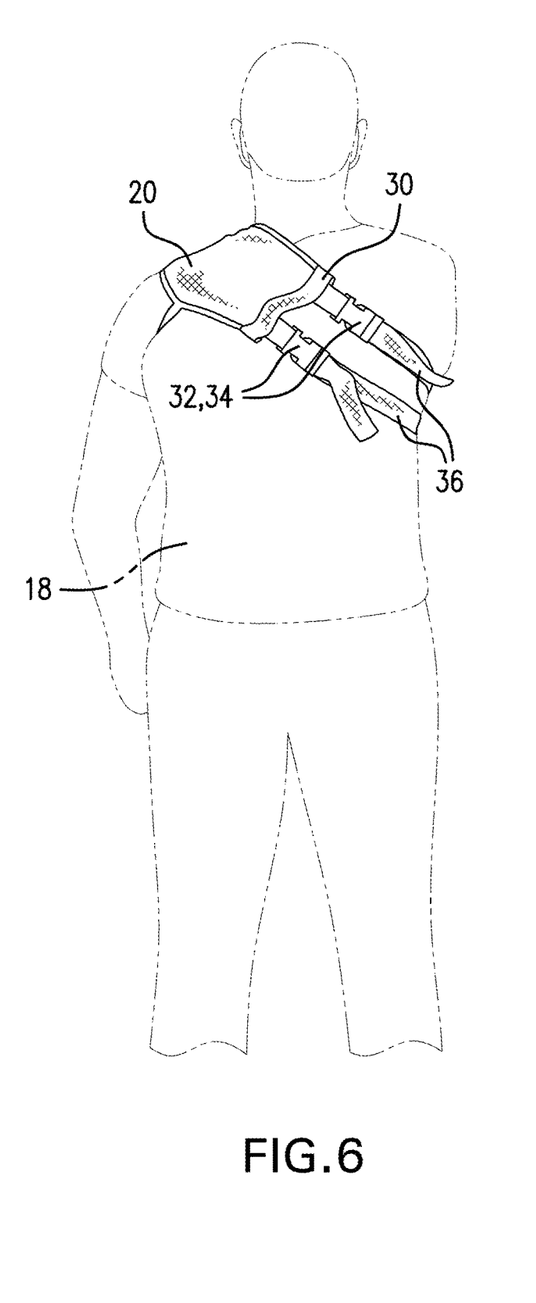
FIG. 6 is a photograph of a rear view of the user of the apparatus of FIG. 1 during use.

FIG. 3 shows the apparatus 20 immobilizing a right arm of the user 18. Specifically, the apparatus 20 secures the right arm to a torso of the user 18. The apparatus 20 secures the right arm in a manner which immobilizes the arm without causing harm to the arm. Furthermore, the arm is secured to the torso and does not get in the way of the user while the user engaging in various activities.

It should be appreciated that the apparatus 20 also provides support for the elbow and shoulder of the user 18. Referring to FIGS. 3 to 6, the support for the right elbow is provided in a manner which lifts the right shoulder to an upright position, and this reduces discomfort to the user as well as minimizes the probability of right shoulder subluxation. Furthermore, the support for the right elbow when placed within the compartment 26 allows the right elbow to be positioned in a resting position which is comfortable for the user. In addition, the main body 22 extends across the torso and across the entire shoulder so as to enable a load (exerted by the arm) to be distributed across the entire shoulder, thus reducing discomfort for the user. Thus, given that discomfort to the user is minimized, the apparatus 20 can be used by the user for prolonged periods of time without adjustment and/or intervention. This is because the design and use of the apparatus 20 allows the user to enjoy ergonomic benefits. In addition, the apparatus 20 also provides the user with a capability to allow positioning of the right arm across the torso of the user to be varied to cater for different types of injuries to the right arm.

Furthermore, the apparatus 20 can also be used in the recovery of, for example, brachial plexus injury, post-obstetric delivery injuries to newborns, flail arm, hemiplegia, spinal cord injuries from C4 and below, mono-neutritis injuries, and so forth. Moreover, the apparatus 20 can be deployed quickly in emergency situations (in both military and civilian scenarios) involving either single or multiple casualties. In addition, the apparatus 20 can be used as an aid to facilitate an independent active lifestyle, whereby the users are able to rely on their free arm to carry out the activities and tasks which they desire, without obstruction by and without causing further injury to their immobilized arm. It should also be noted that the apparatus 20 enables prolonged use with minimal discomfort to the user.

In general, on a holistic level, the apparatus 20 beneficially promote and allow body balance during when users are engaging in physical activities, since it is to be pointed out that conventionally, users with flail arms often lose holistic balance during performance of physical activities.

Finally, the overall posture of the user also improves when using the apparatus 20 as the securing of the apparatus 20 causes an upper portion of the user's torso to be pulled backwards which ensures that the user's back is straightened. This effect on the overall posture alleviates pressure in the user's back and shoulders, thereby minimizing discomfort for the user and enabling prolonged use of the apparatus 20.

Figure 7:
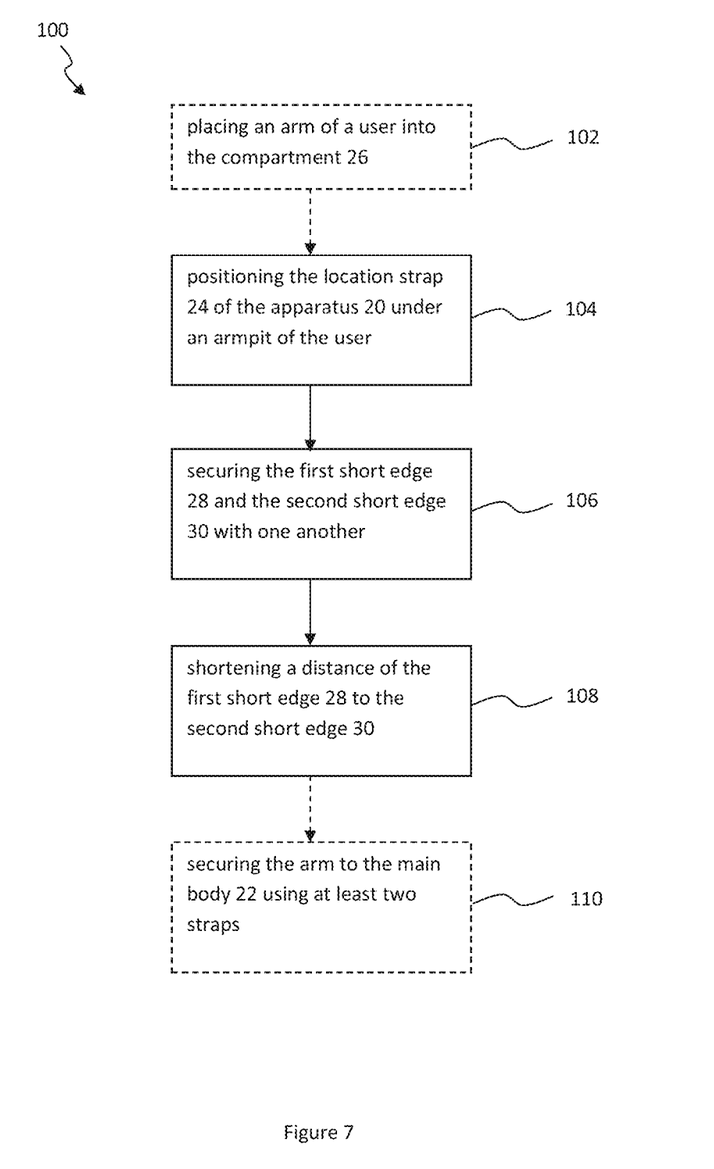
FIG. 7 shows a process flow for a method for wearing the apparatus of FIG. 1.

Referring to FIG. 7, there is shown a method 100 for wearing the arm immobilization apparatus 20. The method 100 comprises placing an arm of a user into the compartment 26 (102); positioning the location strap 24 of the apparatus 20 under an armpit of the user (104); securing the first short edge 28 and the second short edge 30 with one another (106); and shortening a distance of the first short edge 26 to the second short edge 28 (108). It should be appreciated that the method 100 is able to be carried out by a single user without intervention/assistance from third parties. Moreover, it is evident that the user is able to enjoy benefits of the apparatus as described in the preceding paragraphs when wearing the apparatus 20. It should be appreciated that when the apparatus 20 does not include the compartment 26, the method 100 excludes step 102 and includes securing the arm to the main body 22 using at least two straps (110).

Based on the preceding paragraphs, it is noted that the apparatus 20 provides significant improvements compared to known devices, some of which have already been in use for long durations of time without undergoing any enhancements. Given the minimization of discomfort for users of the apparatus 20, it should be appreciated that the apparatus 20 is not a temporary/transient medical device if the user has an arm which is completely/significantly dysfunctional. The apparatus 20 can be a long term aid to enable an active, healthy and independent lifestyle for the user.

The remaining configurations will be described hereinafter. For the sake of brevity, description of like elements, functionalities and operations that are common between the different configurations are not repeated; reference will instead be made to similar parts of the relevant configuration(s).

Figures 8A, 8B:
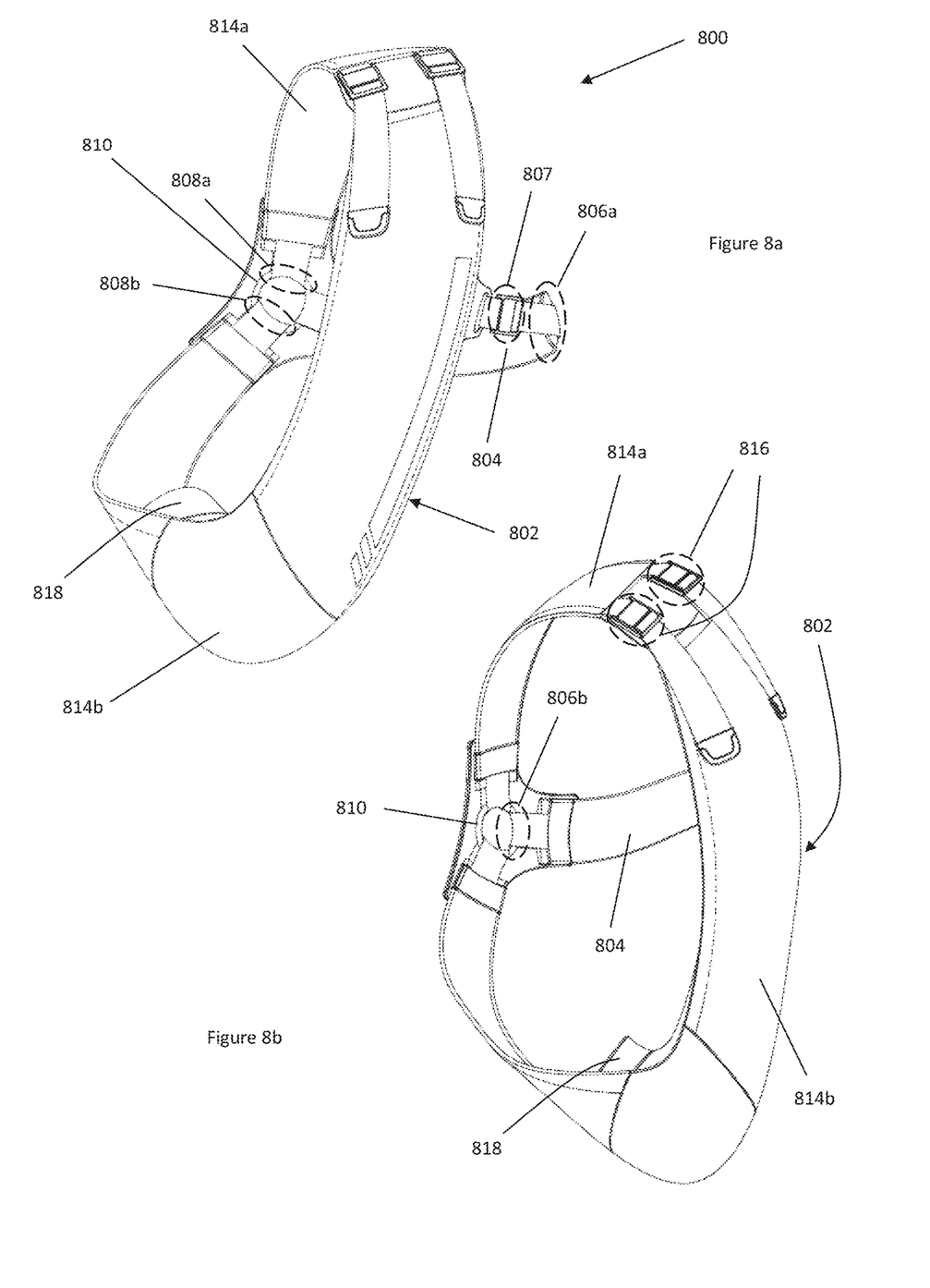
Figure 8C:
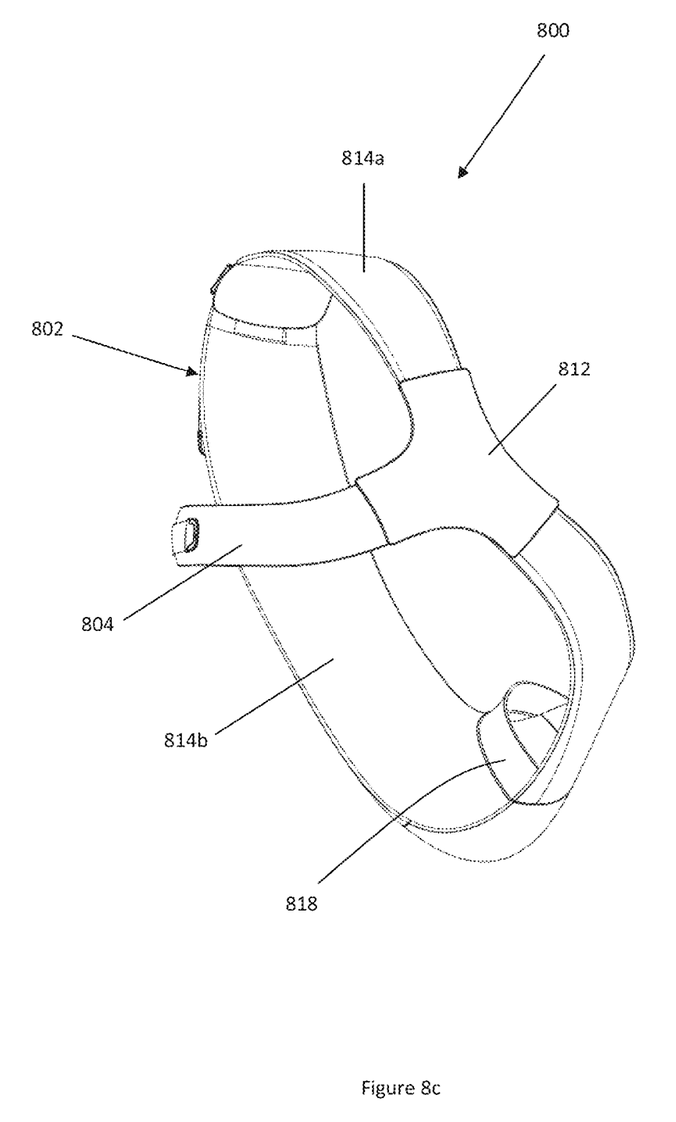
Figure 9A:
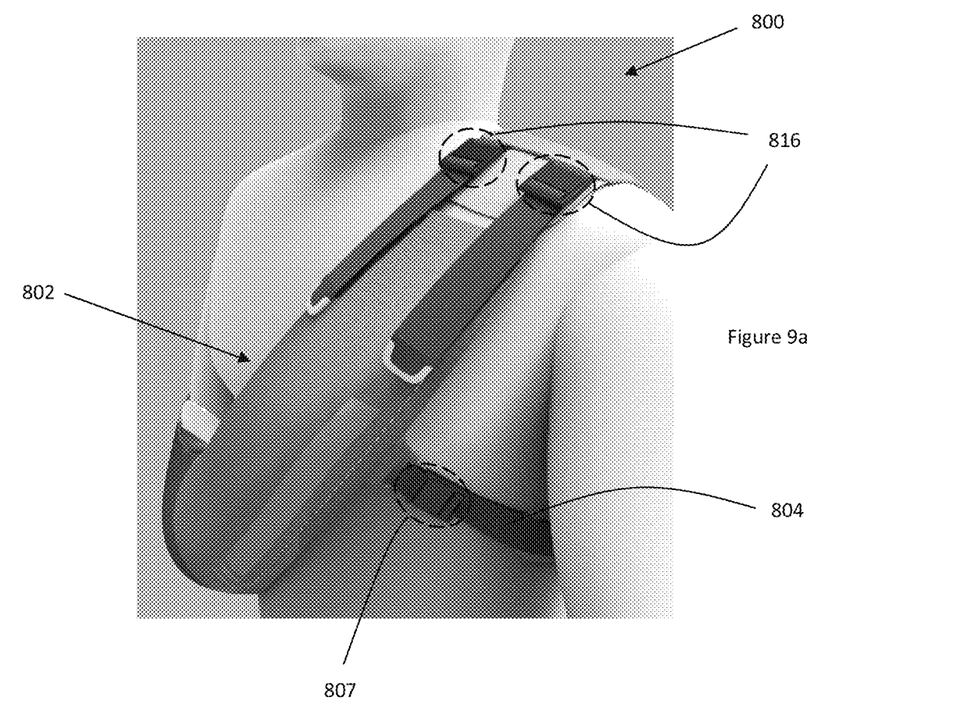
Figure 9B:
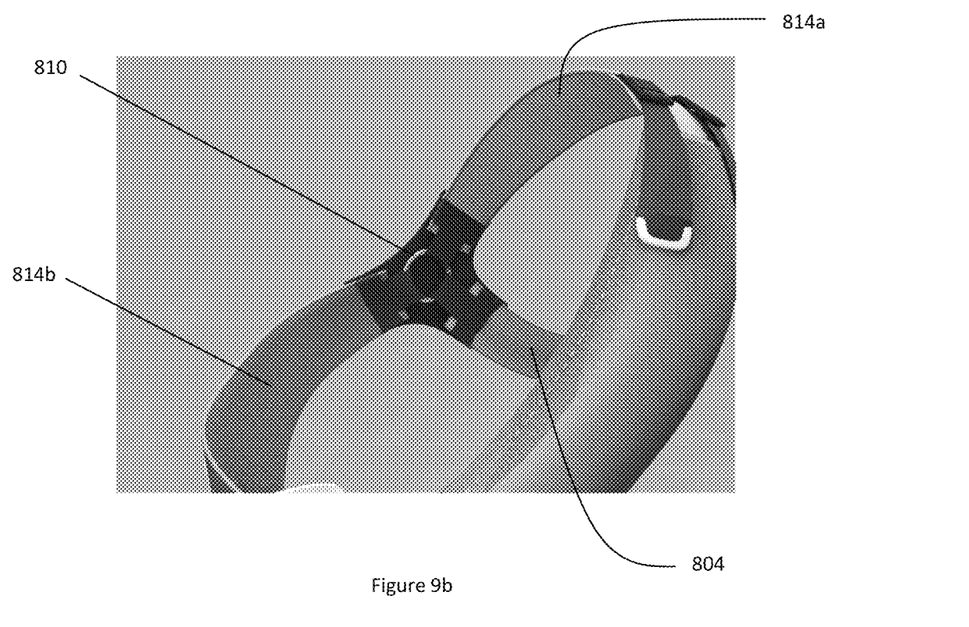
Figure 9C:
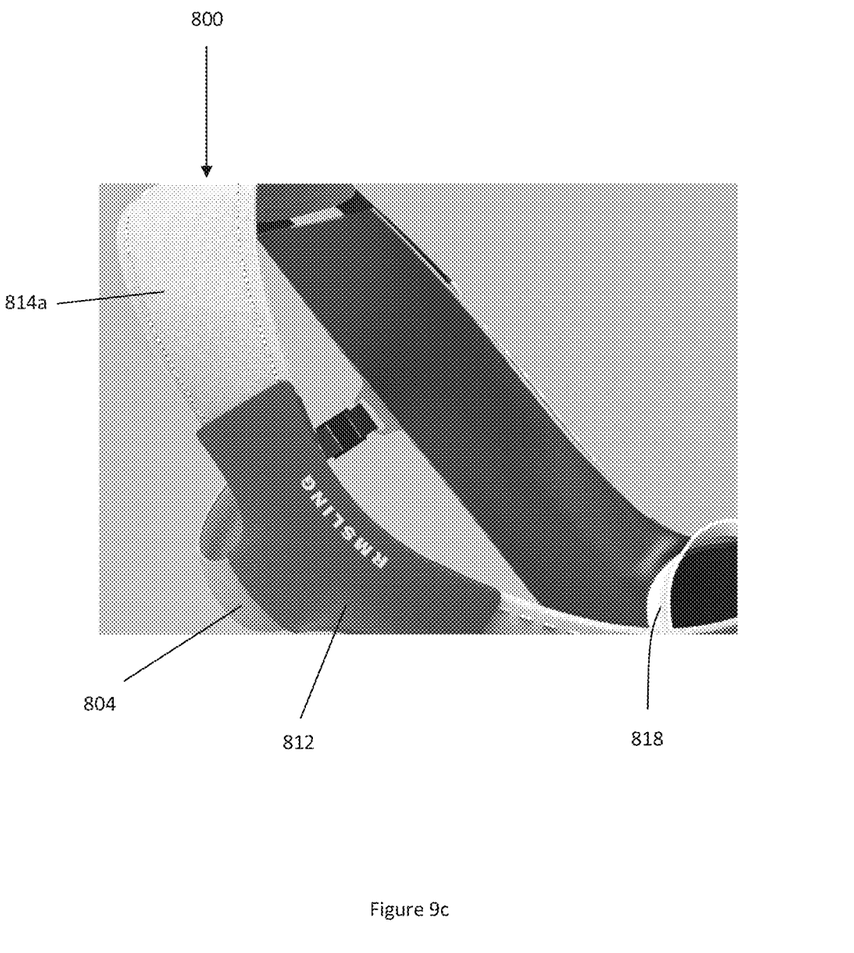

A second embodiment is depicted in FIG. 8, which includes FIGS. 8a-8c respectively showing a front view, a side view, and a back view of an alternative apparatus 800. For completeness, FIG. 9 includes FIGS. 9a-9c showing full image renderings of FIGS. 8a-8c respectively, and where FIG. 9a shows the apparatus 800 being worn on a user. Largely similar to the apparatus 20 of FIG. 1, the apparatus 800 of FIG. 8 has a substantially oblong shape main body 802 and a location strap 804 having first and second ends 806a, 806b. It is to be appreciated that the materials/fabric usable for the main body 802 and location strap 804 are the same as afore described for the apparatus 20 of FIG. 1, and not repeated herein for brevity. The main body 802 has first and second short edges 808a, 808b. Specifically, the first end 806a of the location strap 804 is adjustably coupled to a long edge of the main body 802, and as an example, a quick release device 807 (such as a clip-on fastening device) may be used to enable the first end 806a to be adjustably coupled to the long edge of the main body 802. Hence, the location strap 804 is adjustable length-wise to have a variable length to enable it to be customizable to needs of any user. Then, the second end 806b of the location strap 804 is movably coupled to the first and second short edges 808a, 808b of the main body 802, and in this instance an "O" ring 810 is used for this purpose (but however not to be construed as limiting; other suitable implements are also possible). That is, the "O" ring 810 (functioning as a coupling intersection point) is used to movably couple the second end 806b of the location strap 804, and the first and second short edges 808a, 808b of the main body 802 together, as clearly seen from FIG. 8b.

Moreover, it is to be appreciated that the "O" ring 810 is arranged on the apparatus 800 such that when the apparatus 800 is worn by a user, the "O" ring 810 is positioned at a substantially central portion on the back of the user to enable a more ergonomic and comfortable fit. Also in this embodiment, a distance between the first and second short edges 808a, 808b of the main body 802 is not adjustable (i.e. cannot be shorten/lengthen), unlike in the first embodiment. Nonetheless, it will be understood that the first short edge 808a of the main body 802 is coupled to the second short edge 808b of the main body 802. It is to be highlighted that the arrangement of using the "O" ring 810 provides a certain degree of movement to the location strap 804 (via being slidably movable around on at least a portion of the "O" ring 810), and so when the apparatus 800 is worn by a user, flexibility in terms of enabling the apparatus 800 to provide an improved and more comfortable fit to the said user is granted by the movable location strap 804. It is also to be appreciated that a comfort padding 812 (or the like) of a suitable size and shape may be used to provide a support backing for the portion of the apparatus 800, at where the coupling intersection point formed by the "O" ring 810 is located. Further, the comfort padding 812 may collectively hide the "O" ring 810, the second end 806 of the location strap 804, and the first and second short edges 808a, 808b of the main body 802, so that the back of the apparatus 800 appears visually tidy.

In addition, the main body 802 of the apparatus 800 comprises first and second portions 814a, 814b, in which at least the first portion 814a is adjustably coupled to the second portion 814b to enable an overall length of the main body 802 to be configurable. In FIG. 8a, it may be seen that the first portion 814a is the relatively shorter portion that forms the main body 802, as compared to the second portion 814b. Also, one end of the first portion 814a forms the first short edge 808a of the main body 802, whereas one end of the second portion 814b then forms the second short edge 808b of the main body 802. The respective ends of the first and second portions 814a, 814b which are not the first and second short edges 808a, 808b are then coupled to each other via at least one fastening device 816 (e.g. a strap adjustment device), as seen from FIGS. 8a and 8b. It is to be appreciated that the fastening device 816 may also be termed as a shoulder clip (or any similar terminology), since the fastening device 816 is arranged (on the apparatus 800) to be substantially located near the shoulder of a user for convenient adjustment. In this case, the definition of at least one fastening device 816 includes two of such fastening devices 816, but is not to be construed as limiting. Further, the second portion 814b includes (at least one) elastic band 818 that is arranged transversely to the length of the second portion 814b, and the purpose of the elastic band 818 is to releasably secure and immobilize an arm of a user (of the apparatus 800) to a sleeve compartment formed in the main body 802, when the apparatus 800 is being worn. The sleeve compartment enables the arm of the user to be placed and secured thereinto with the help of the elastic band 818. It is to be appreciated that when the apparatus 800 has been worn, and the arm of the user is immobilized in the sleeve compartment of the main body 802, the immobilized arm is held in an angled position which is at about 45° relative to (the vertical axis of) the body of the user.

Figure 10:
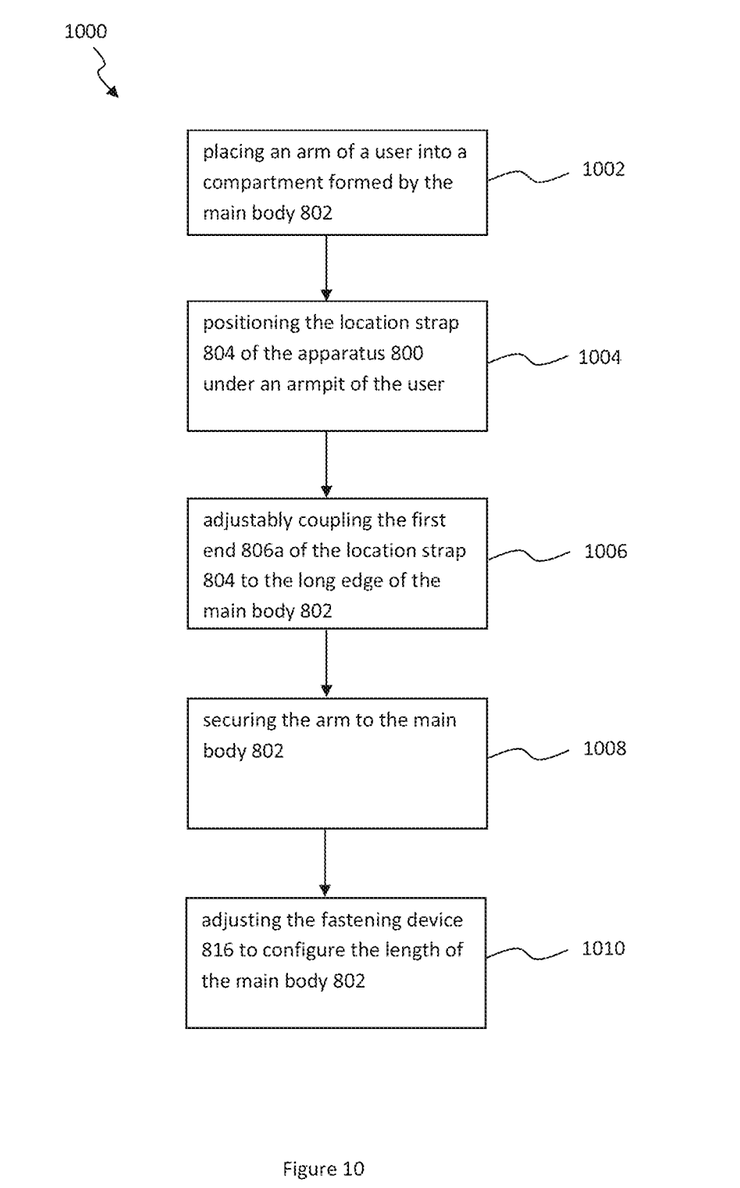
FIG. 10 shows a process flow for a method for wearing the apparatus of FIG. 8.

With reference to FIG. 10, it is to be appreciated that a corresponding method 1000 for wearing the apparatus 800 comprises placing (1002) an arm of a user into the sleeve compartment formed by the second portion 814b of the main body 802; positioning (1004) the location strap 804 of the apparatus 600 under an armpit of the user; adjustably coupling (1006) the first end 806a of the location strap 804 to the long edge of the main body 802; and securing (1008) the arm of the user to the main body 802. In addition, subsequent to step 1008, the user may also optionally adjust the fastening device 816 (in step 1010) to obtain a better fit of the apparatus 800 mounted on the body of the user, through suitably configuring the length of the main body 802. It is also to be appreciated that there is an intermediate step (not shown in FIG. 10) subsequent to step 1002, but prior to step 1004—this intermediate step comprises looping the apparatus 800 overhead the user and onto the body of the user, so that the main body 802 is now positioned across the body of the user, and the first and second short edges 808a, 808b of the main body 802 are positioned at the rear of the user's body. Once the apparatus 800 is looped over the user's head and worn with the injured arm held in the sleeve compartment, the remaining steps 1004-1010 can then be performed. In other words, this intermediate step can broadly be defined as wearing the main body 802 on the body of the user. Advantageously, it is to be appreciated that the method 1000 may be performed by a single user without intervention/assistance from third parties, and compared to the apparatus 20 of FIG. 1, it is even easier for a user to wear the apparatus 800 of FIG. 8 by himself since convenient adjustment of the quick release device 807 at the front of the user's body (as opposed to from the rear of the user's body) is all that is required, after the apparatus 800 has been worn on his body. Indeed, the apparatus 800 of FIG. 8 makes for easier mounting onto a user's body, since there is no necessity to now wear the location strap, unlike in the first embodiment. Moreover, as explained, the apparatus 800 of FIG. 8 enables a relatively much easier adjustment of the location strap 804 (via the quick release device 807) and the length of the main body 802 (via the fastening device 816) from the front of the user's body, rather than from the rear of the user's body, which may suffer from inconvenient usage as will be appreciated.

Figure 11A:
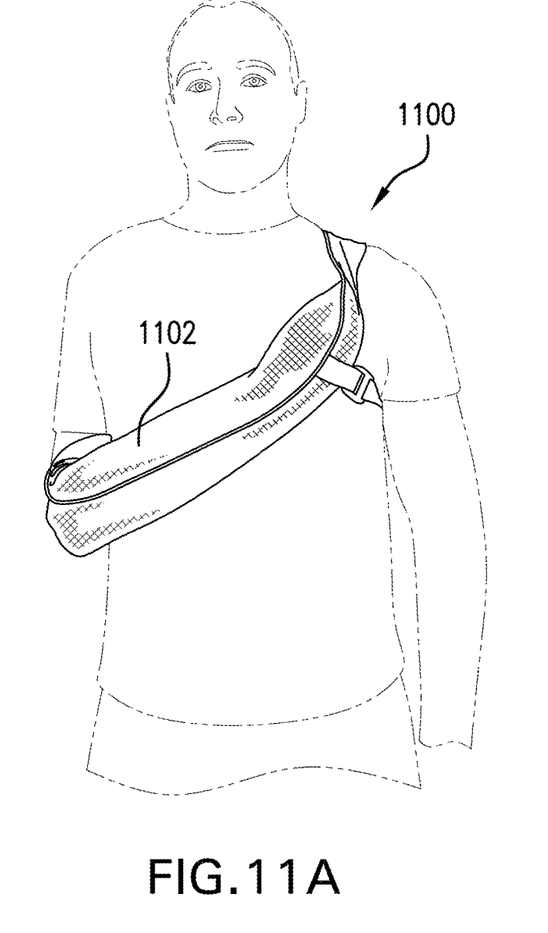
Figure 11B:
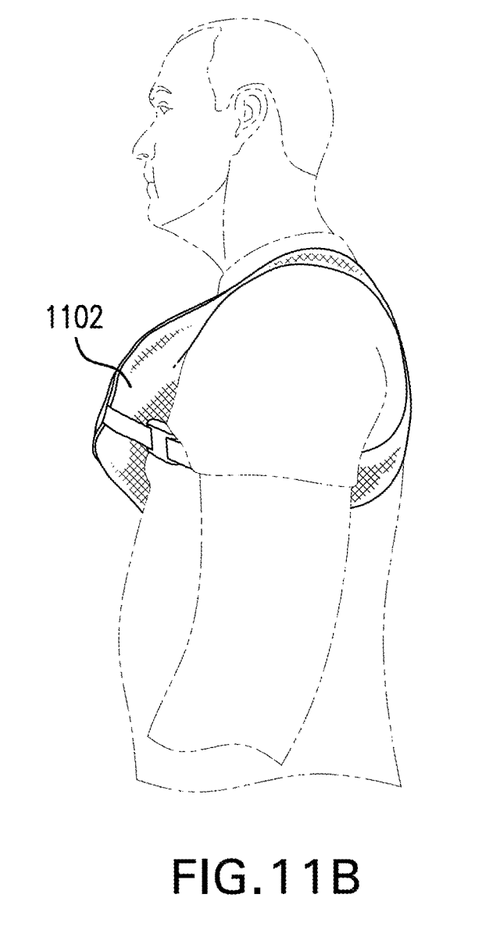
Figure 11C:
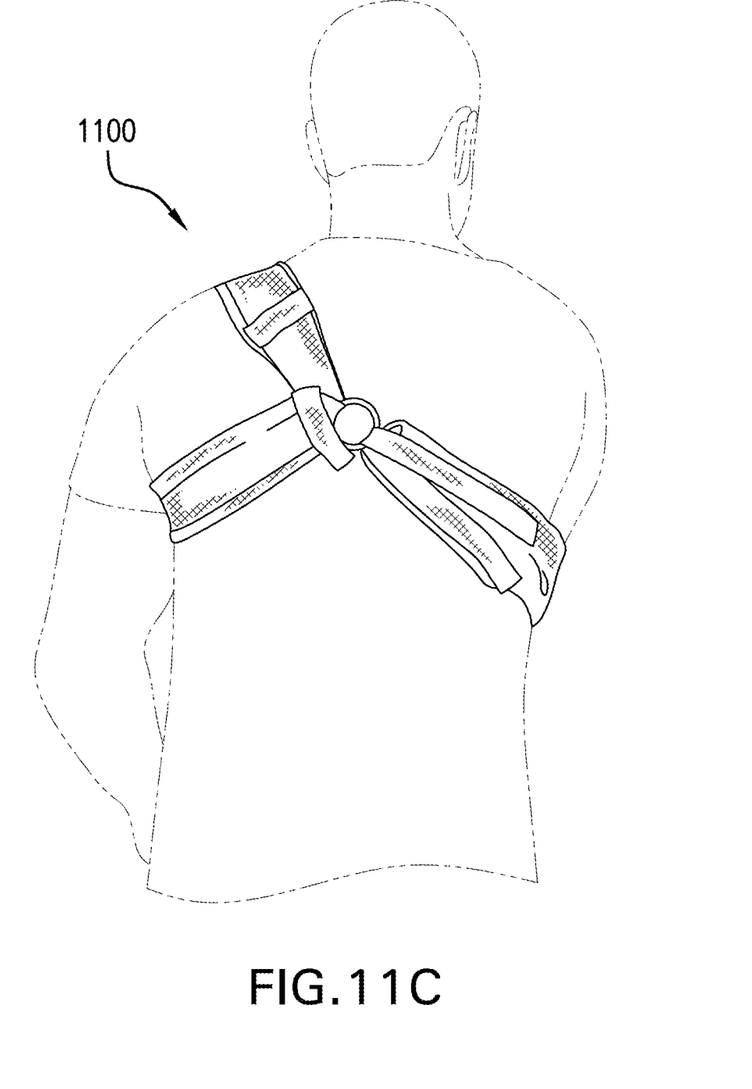
Figure 12:
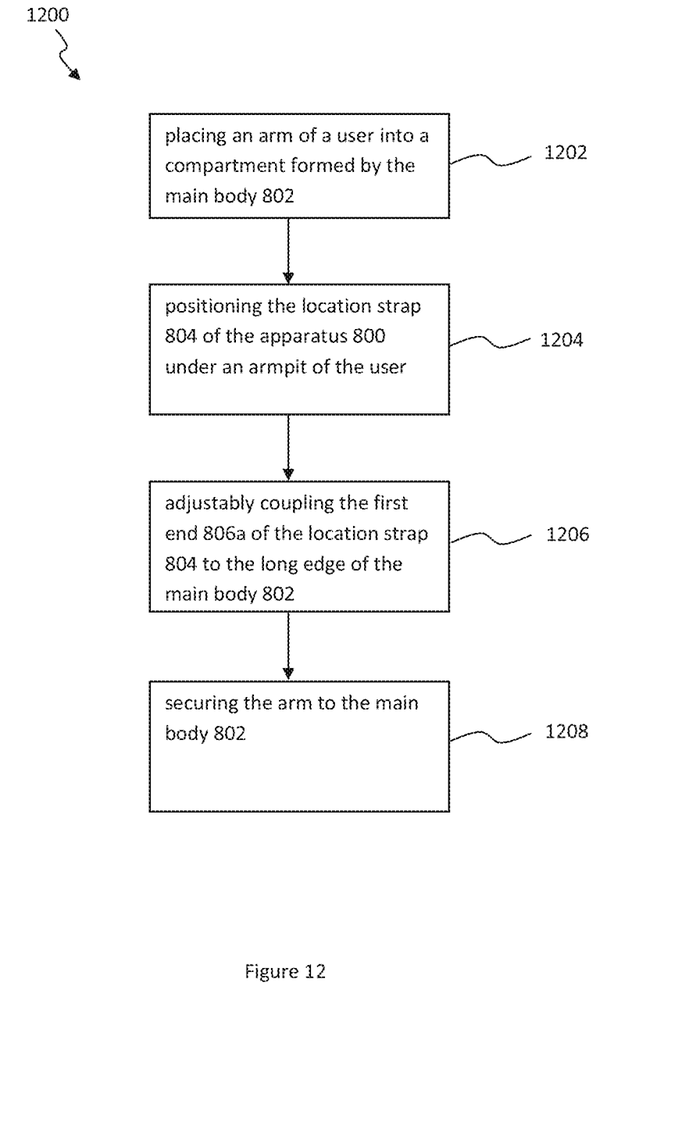
FIG. 12 shows a process flow for a method for wearing the apparatus of FIG. 11.

A third embodiment is depicted in FIG. 11, which includes FIGS. 11a-11c respectively showing a front view, a side view, and a back view of another variant apparatus 1100. Basically, the apparatus 1100 of FIG. 11 is largely the same in construction as the apparatus 800 of FIG. 8, except that a main body 1102 of the apparatus 1100 in this embodiment is now integrally formed (i.e. the main body 1102 is made from a contiguous piece of material as a whole), instead of comprising the first and second portions 814a, 814b set out in the second embodiment. This means that the main body 1102 of the apparatus 1100 is therefore not configured with an adjustable length. FIG. 12 shows a corresponding method 1200 for wearing the variant apparatus 1100, and it will be seen that FIG. 12 is largely similar to FIG. 10, except that a step corresponding to the last step 1010 is missing. That is to say, the method 1200 of FIG. 12 omits the step of needing a user to optionally adjust the fastening device 816 to obtain a better fit of the apparatus 800 mounted on the body of the user, since the main body 1102 of the apparatus 1100 is integrally formed. Separately, steps 1202-1208 of the method 1200 correspond respectively to steps 1002-1008 of the method 1000, and so for brevity sake, descriptions for steps 1202-1208 are not repeated here.

It is to be appreciated that both the apparatuses 800, 1100 of FIGS. 8 and 11 are developed for users with less active needs, as compared to the first embodiment. Also, it is to be highlighted that apparatuses 800, 1100 of FIGS. 8 and 11 also share the same afore described advantages of the apparatus 20 of the first embodiment, and hence will not be repeated here.

Whilst there have been described in the foregoing description preferred embodiments of the present invention, it will be understood by those skilled in the technology concerned that many variations or modifications in details of design or construction may be made without departing from the present invention. For example, in the second embodiment, the second end 806b of the location strap 804 need not be movably coupled to the first and second short edges 808a, 808b of the main body 802—instead, the second end 806b of the location strap 804 can be fixedly attached to both the first and second short edges 808a, 808b of the main body 802 for a simpler arrangement. Hence, the "O" ring 810 (or other equivalent implements) is not required under such a variation.

In addition, for certain variant embodiments, the location strap 804 need not be adjustably coupled to the long edge of the main body 802—instead, the first end 806a of the location strap 804 is simply fixed to the long edge of the main body, and hence there is then no need for the quick release device 807. Further alternatively, the first end 806a of the location strap 804 may configured to be dynamically mountable to different desired multiple positions along the long edge of the main body 802, which beneficially provides a better comfortable fit of the location strap 804 to different users' bodies, according to their respective body sizes. Hence, different mounting points (not shown) are provided and spaced along the long edge of the main body 802 to enable the said variant feature described in the preceding sentence. Separately, the fastening device 816 may also be arranged to permit a greater range of adjustment in order that an immobilized arm may rest at an angled position which is between about 60° to 90° position relative to (the vertical axis of) the body of an associated user.

It is to be pointed out that broadly, a method of wearing the apparatuses 800, 1100 of FIGS. 8 and 11, along with the variant features described in the immediate preceding paragraph, may include the following steps: placing an arm of a user into the compartment; wearing the main body 802 on the body of the user; and positioning the location strap 804 of the apparatus 800, 1100 under an armpit of the user, or alternatively, may instead include positioning the location strap 804 of the apparatus 800, 1100 under an armpit of a user; wearing the main body 802 on the body of the user; and securing the arm of the user to the main body 802.

The invention claimed is:

1. An arm immobilization apparatus comprising:
    a main body arranged to be of a substantially oblong shape, the main body comprising a long edge, a first short edge and a second short edge, the first short edge and the second short edge being formed at opposing ends of the main body; and
    a location strap having first and second ends,
    wherein the first end of the location strap is arranged to be coupled to the long edge of the main body, and the second end of the location strap is coupled to both the first and second short edges of the main body.

2. The apparatus of claim 1, wherein the first end includes being adjustably couplable to the long edge of the main body.

3. The apparatus of claim 2, further including a quick release device at the first end to enable the first end to be adjustably couplable to the main body.

4. The apparatus of claim 2, wherein the main body is integrally formed.

5. The apparatus of claim 1, further including a compartment for placement of an arm of a user of the apparatus.

6. The apparatus of claim 5, wherein the compartment is formed using a non-stretchable fabric or a stretchable fabric configured to enable dissipation of heat from within the compartment.

7. A method for wearing the arm immobilization apparatus of claim 5, the method comprising:
    placing an arm of a user into the compartment;
    wearing the main body on the body of the user, wherein the main body is positioned across a torso and a shoulder of the body of the user;
    positioning the location strap of the apparatus under an armpit beneath the shoulder of the user on an opposite side of the arm being immobilized; and
    adjustably coupling the first end of the location strap to the long edge of the main body to mount the arm immobilization apparatus to the torso of the user.

8. The apparatus of claim 1, wherein the second end includes being movably coupled to the first and second short edges of the main body.

9. Apparatus of claim 8, wherein the second end is movably coupled to the first and second short edges of the main body via a ring.

10. The apparatus of claim 1, wherein the main body comprises first and second portions, in which at least the first portion is adjustably coupled to the second portion to enable a length of the main body to be configurable.

11. The apparatus of claim 10, wherein the first and second portions include at least one fastening device respectively.

12. The apparatus of claim 1, wherein the second end includes being attached to the first and second short edges of the main body.

13. The apparatus of claim 1, wherein the first short edge of the main body is configured to be coupled to the second short edge of the main body.

14. The apparatus of claim 1, wherein the location strap has a variable length.

15. The apparatus of claim 1, wherein the main body is fabricated from a hard-wearing, lightweight and flexible fabric.

16. The apparatus of claim 1, wherein the location strap is configured for mounting the apparatus in multiple positions.

17. The apparatus of claim 1, further comprising at least one device configured to carry out at least one task for determining a condition or a state of activity of a user of the apparatus.

18. A method for wearing the arm immobilization apparatus of claim 1, the method comprising:
    positioning the location strap of the apparatus under an armpit beneath a shoulder of a user on an opposite side of the arm being immobilized;
    wearing the main body on the body of the user, wherein the main body is positioned across a torso and the shoulder of the body of the user;
    securing the arm of the user to the main body; and
    adjustably coupling the first end of the location strap to the long edge of the main body to mount the arm immobilization apparatus to the torso of the user.

* * * * *